(12) United States Patent
Melendez et al.

(10) Patent No.: US 8,143,231 B1
(45) Date of Patent: Mar. 27, 2012

(54) METHOD OF REDUCING HIV-REPLICATION IN HUMAN BODY TISSUE

(75) Inventors: Loyda M Melendez, Guaynabo, PR (US); Claribel Luciano-Montalvo, Guayanilla, PR (US)

(73) Assignee: University of Puerto Rico, San Juan, PR (US)

( * ) Notice: Subject to any disclaimer, the term of this patent is extended or adjusted under 35 U.S.C. 154(b) by 421 days.

(21) Appl. No.: 12/460,576

(22) Filed: Jul. 20, 2009

Related U.S. Application Data (60) Provisional application No. 61/081,769, filed on Jul. 18, 2008.

(51) Int. Cl.
    *A61K 31/70*     (2006.01)
    *A61K 31/00*     (2006.01)
    *C07H 21/04*     (2006.01)

(52) U.S. Cl. ............... 514/44; 514/1; 536/24.5

(58) Field of Classification Search .......... None
See application file for complete search history.

(56) References Cited

OTHER PUBLICATIONS

Venkataraman et al. Journal of Immunology 2005, vol. 175, pp. 7560-7567.*
Ciborowski et al. Virology 2007, vol. 363, pp. 198-209.*

* cited by examiner

*Primary Examiner* — Tracy Vivlemore
(74) *Attorney, Agent, or Firm* — Hoglund & Pamias, PSC; Roberto J. Rios

(57) ABSTRACT

Mononuclear phagocytes are reservoirs, vehicles of dissemination, and targets for persistent HIV infection. However, not all MP population equally support viral growth. Such differential replication is typified by the greater ability of placental macrophages (PM), as compared to blood borne monocyte-derived macrophages (MDM), to restrict viral replication. A SELDI-TOF protein peak with an m/z of 11,100 identified as cystatin B (CSTB), was significantly lower in uninfected and HIV-infected PM than in MDM. HIV replication can be reduced by down regulating the expression of Cystatin B.

3 Claims, 6 Drawing Sheets

| Peak | Peak Median m/z[a] | Peak Intensity in PM | Peak in PM-HIV |
|---|---|---|---|
| 1 | 5037 | ↑ | ↑ |
| 2 | 5232 | ↑ | ↑ |
| 3 | 5644 | − | ↓ |
| 4 | 5680 | ↓ | ↓ |
| 5 | 5815 | − | ↓ |
| 6 | 5913 | ↓ | ↓ |
| 7 | 7699 | ↓ | ↓ |
| 8 | 7890 | ↑ | − |
| 9 | 9193 | ↓ | ↓ |
| 10 | 9550 | − | ↓ |
| 11 | 9905 | ↓ | ↓ |
| 12 | 10,098 | ↓ | ↓ |
| 13 | 10,216 | ↓ | ↓ |
| 14 | 10,330 | − | ↓ |
| 15 | 10,582 | − | ↓ |
| 16 | 10,776 | ↓ | ↓ |
| 17 | 10,959 | ↓ | ↓ |
| 18 | 11,101 | ↓ | ↓ |
| 19 | 11,289 | ↓ | ↓ |
| 20 | 11,878 | − | ↑ |
| 21 | 12,214 | ↑ | ↑ |
| 22 | 12,344 | ↑ | ↑ |
| 23 | 12,430 | ↑ | ↑ |
| 24 | 13,623 | ↑ | ↑ |
| 25 | 14,545 | ↑ | − |
| 26 | 15,013 | ↓ | ↓ |
| 27 | 15,790 | ↑ | ↑ |

FIG. 2

| SELDI-TOF, m/z[a] | Molecular Weight | MDM | PM | MDM-HIV | PM-HIV | Protein Name |
|---|---|---|---|---|---|---|
| 9905 | 9987 | NF | 2 | NF | NF | Cytoskeletal 14-like protein |
| 10,330 | 10,438 | 2 | NF | NF | NF | SH3 glutamic acid rich-like protein 3 |
| 10,776 | 10,835 | NF | NF | 2 | NF | Protein S-100 A8 (Calgranulin A) |
| 10,959 | 10,932 | 2 | 2 | 2 | 2 | 10 Kda heat shock protein |
| 11,101 | 11,139 | 4 | 2 | 4 | 3 | Cystatin B |
| 11,289 | 12 | 2 | 2 | 2 | 2 | Cytochrome C |
| 12,344 | 12,774 | 4 | NF | 4 | NF | SH3 glutamic acid rich-like protein 1 |
| 12,430 | 12,895 | NF | 2 | 2 | NF | Myotrophin |
| 13,623 | 13,242 | NF | NF | 2 | 2 | Protein S-100 A9 (Calgranulin B) |
| 14,545 | 14,716 | NF | NF | 2 | NF | Galectin-1 |
| 15,013 | 15,054 | 5 | 6 | 5 | 5 | Profilin |
| 15,790 | 15,936 | 2 | NF | NF | 2 | Superoxide dismutase CuZn |

METHOD OF REDUCING HIV-REPLICATION IN HUMAN BODY TISSUE

FEDERAL GRANTS

This research was supported, in part by the National Institute of Health through their NINDS U54NS430, NIGMS MBRS-SCORE-SO6GMO822, NCRR-RCMI-CRC P20RR11126, RCM-G12RR03051, and MBRS-RISE GM61838 grants. The Government has certain rights in this invention.

BACKGROUND OF THE INVENTION

Mononuclear phagocytes (MP; monocytes, tissue macrophages, and dendritic cells) are reservoirs and vehicles for HIV dissemination in the infected human host. Understanding HIV dynamics in resident MP is important since viral sequestration in tissue occurs as a consequence of disease progression.

One body tissue in which restricted infection of MP and virus compartmentalization can occur is the placenta. Trophoblasts are susceptible to infection but show restricted viral replication, whereas productive viral infection occurs in placental macrophages (PM). Interestingly, the levels of HIV replication in PM are at least 10-fold lower than what is seen in peripheral blood monocyte-derived macrophages (MDM. Decreased CCR5 expression has been associated with restricted HIV replication in PM, but the intracellular mechanisms that affect it are not known.

Previously, several host factors were identified to be associated with HIV restriction in the placenta. Leukemia inhibitory factor (LIF) is a placenta-secreted protein that limits viral replication in the placenta. The pregnancy-related hormone human chorionic gonadotropin beta-subunit (b-hCG) is produced by trophoblasts and upon addition to placenta explants inhibits HIV expression and progeny virion production. hCG inhibited HIV RT and p24 antigen from HIV-infected lymphocytes when they were co-cultured with placental trophoblasts. A dose-dependent inhibition of HIV infection in hCG-treated tissue explants was found. Correlations were made between hCG concentrations in blood and viral load or HIV infection. However, it was unknown which host factors account for PM infection and viral growth.

SUMMARY OF THE INVENTION

Thus, according to an aspect of the invention a proteomics approach was applied to identify cellular protein(s) associated with restricted HIV replication in PM.

According to another aspect of the invention, the low molecular proteome of HIV-infected PM and MDM were compared and protein candidates associated with viral replication were identified. A proteomics approach according to the invention consisted of surface-enhanced laser desorption/ionization time-of-flight mass spectrometry (SELDI-TOF MS), 1D-gel electrophoresis, liquid chromatography tandem MS (LC-MS/MS), and Western blot.

According to a further aspect of the invention, 12 proteins were identified that correlate with SELDI-TOF protein profiling by LC-MS/MS.

In another aspect of the invention, the expression of cystatin B (CSTB) was validated by Western blot. (CSTB) was differentially expressed between uninfected and HIV-infected PM and MDM. Lower CSTB was observed in PM than in MDM by Western blot assays.

According to another aspect of the invention, application of siRNA for CSTB to MDM, demonstrated that reduced CSTB was associated with decreased HIV replication. Reducing CSTB contributes to the innate resistance to HIV PM infection and protects against maternal-fetal viral transmission of surface-enhanced laser desorption/ionization time-of-flight mass spectrometry (SELDI-TOF MS), 1D-gel electrophoresis, liquid chromatography tandem MS (LC-MS/MS), and Western blot. We identified 12 proteins that correlate with SELDI-TOF protein Profiling by LC-MS/MS. Of these we chose to validate the expression of cystatin B (CSTB) by Western blot because it was differentially expressed between uninfected and HIV-infected PM and MDM. Importantly, previous studies have associated this protein with HIV-infected MDM. Lower CSTB was observed in PM than in MDM by Western blot assays. By applying siRNA for CSTB to MDM, we demonstrated that reduced CSTB was associated with decreased HIV replication. Our studies suggest that reduced CSTB contributes to the innate resistance to HIV PM infection and thereby protects against maternal-fetal viral transmission.

The present invention compares the low molecular proteome of HIV-infected PM and MDM and identifies protein candidates associated with viral replication.

BRIEF DESCRIPTION OF THE DRAWINGS

FIG. 5b illustrates a Bar chart showing the respective statistical analysis information of the Western Blot Plotting of FIG. 5a.

DETAILED DESCRIPTION OF THE INVENTION

The invention will be described in accordance with the following description and the accompanying Figures.

For the Isolation an cultivation of PM and MDM, full-term placentas from HIV-1, HIV-2, and hepatitis B seronegative women were obtained from the University of Puerto Rico Hospital in Puerto Rico. Placentas were perfused for 45 min as previously described. PM were seeded at a concentration of 1×106 cells/mL in a total volume of 30 mL and supplemented with RPMI 1640 containing 20% fetal bovine serum, 10% human serum (Sigma), 100 U/mL pen/strep (Sigma), and 2 mM glutamine (Sigma). Non-adherent cells were removed 7 days after seeding.

Peripheral blood monocytes were obtained from leukapheresis and centrifugal elutriation of HIV-1, HIV-2, and hepatitis B seronegative donors as previously described. Monocytes were seeded at the same concentration as that of the PM. MDM were obtained after 7 days of culture in Dulbecco's modified Eagle's media (DMEM) supplemented with 10% heat-inactivated pooled human sera, 50 µg/mL gentamicin, 10 µg/mL ciprofloxacin (all from Sigma), and 1000 U/mL macrophage colony-stimulating factor (MCSF).

HIV infection of PM and MDM were achieve after 7 days in culture, PM and MDM were inoculated with 25 ng of HIV-1$_{BaL}$ per 2×105 cells, as previously described. After 1 h of incubation at 37° C., virus was removed by washing with media. Culture fluids were collected at 0, 2, 4, 6, 9, and 12 days, centrifuged, and stored at −80° C. for determinations of HIV-1 p24 antigen levels by ELISA following the manufacturer's instructions. Seven days after infection, cells were harvested for SELDI-TOF assays. Six placentas and three MDM were maintained for 6 days post-infection and four PM and MDM from different donors were cultured for 12 days and compared to uninfected controls. Values for HIV infection are presented as log p24 antigen+/−SD. Cultures were monitored for cytopathic effects.

The preparation of the cell lysates was prepared 6 days after viral infection. Cells were washed and cultured for an additional 12-16 h in media without sera. Cells were washed with cold PBS and incubated on ice for 15 min with lysis buffer (5 mM Tris-HCl buffer, pH 8.0, 0.1% Triton X-100, and protease inhibitor (Sigma)). Lysates were cleared by centrifugation for 10 min at 1700 rpm at 4° C., and stored at −80° C. for further analyses. Protein concentration was measured using BioRad DC Protein Assay.

SELDI-TOF analysis was performed to profile proteins of uninfected and HIV-infected PM and MDM cell lysates cultured for 6 days post-infection. We used weak cation-exchange (CM-10) and the strong anion-exchange (Q-10). A total of 50 µL of protein sample (0.1 µg/µL) was applied per spot and tested in quadruplicates. Binding buffer, sample deposition, and analysis procedure were the same as previously reported with minor modifications. The ProteinChip® reader was externally calibrated for each analysis using mixtures of four standard proteins: bovine insulin (5733Da), cytochrome C (12,230Da), superoxide dismutase (15,591Da), and beta-lactoglobulin (18,363Da).

In order to identify the protein, 20 µg of protein was hydrated with NuPAGE® LDS buffer, and then separated by one-dimensional electrophoresis on a NuPAGE® Novex 10% bis-Tris gel. Proteins were stained with Coomassie BB. Bands corresponding to SELDI-TOF spectral regions were cut from the gel with a sterile razor blade. After de-staining with 50% ACN, 50 mM NH$_4$HCO$_3$/50% ACN, and 10 mM NH$_4$HCO$_3$/50%, the gel pieces were dried and proteins subjected to in-gel trypsin digestion for 12-16 h. Resulting peptides were extracted using a mixture of 40% H$_2$O, 60% ACN, and 0.1% trifluoroacetic acid. Samples were dried and resuspended in 12 µL of water and 0.1% formic acid prior to LC-MS/MS analysis. Data obtained from LC-MS/MS analysis were searched against the NCBI Fasta protein database narrowed to a subset of human proteins using the Sequest algorithms 3.1SR software from Thermo Electron Corporation. Protein identifications were accepted as true positives if the following criteria were met: $X_{corr}$ for doubly charged precursor ion>2.5, DeltaCn≧0.3, more than 60% of fragment ions per sequenced peptides, and at least two peptides per identified protein.

For the Western blot analyses, twenty micrograms of PM and MDM lysates from seven different donors was diluted with Laemmli sample buffer, and applied to a 4-20% Tris-HCl Ready Gel well and transferred to 0.45 µm nitrocellulose membranes. After blocking with 3% BSA in TBS, the membrane was incubated with goat cystatin B (n=4, 1:500) and sheep SOD antibodies (n=3, 1:2000) followed by incubation with the corresponding secondary antibody conjugated with horseradish peroxidase (HRP). Mouse β-actin antibody was used as the loading control. The U87 human glioblastoma whole cell lysate was used as the positive control for cystatin B and the HeLa whole cell lysate for SOD. Signal was detected using the Visualizer™ Chemiluminescent Substrate HRP detection system. The density of protein bands was determined using the Versa Doc System with Quantity One Software and normalized against β-actin.

In order to carry out the siRNA studies the following materials were used: irrelevant siRNA used as negative control (control siRNA); the siRNA against CSTB (CSTB siRNA); and Dharmafect 4 acting as a transfection reagent. The percentage of viable cells in experimental and control cultures was determined prior to in vitro infection. Briefly, MDM (1.25×10$^5$) were cultured in 96-well plates and the viability in control siRNA, CSTB siRNA-treated and HIV-infected cells were compared to uninfected untreated controls using 3-(4, 5-dimethylthiazol-2-yl)-2,5-diphenyltetrazolium bromide (MTT). On day 6 after infection, MDM were washed with monocyte media followed by the addition of 0.5 µg/mL of MTT to each well. Cells were incubated at 37° C. for 4 h and thereafter 100 µL of DMSO was added for 15 min at room temperature. Absorbance was measured at 570 nm. Viability for control siRNA, CSTB siRNA, and HIV-infected cells was expressed as percentages of the uninfected and untreated cells.

To determine the effect of CSTB on HIV infection, this protein was inhibited from MDM cultures by using small interference RNA (siRNA). Briefly, monocytes were seeded at 1×10$^7$ cells in 25-mm$^2$ plates and differentiated into MDM for 7 days in DMEM containing MCSF. After differentiation, cells were incubated in antibiotic free medium overnight with 5% CO$_2$ and transfected with 100 nM of control siRNA, or CSTB siRNA. Cells were incubated for 24 h in monocyte media after siRNA removal. In vitro infection was done with HIV-1$_{BaL}$ at a concentration of 25 ng/mL (MOI of 0.1) after 24-h of siRNA removal. HIV infection was allowed to proceed for days and supernatant collected to measure HIV p24 antigen levels. Whole cell lysates were prepared as described for Western blotting. To determine inhibition of HIV in silenced CSTB samples, p24 antigen levels from three independent control experiments (control siRNA) were determined and expressed as 100% infection. These experiments were performed on MDM cultures from three different donors. The mean of each independent p24 antigen value in CSTB siRNA was expressed as a percentage of its respective control siRNA, as reported previously.

Analysis of variance (ANOVA) was applied with specimen type and days of infection to compare levels of HIV replication. For SELDI-TOF data analysis, the spectrum obtained was analyzed with an integral statistical software program specifically designed for the ProteinChip®. The parameters for peak detection were first pass signal/noise (S/N) ratio=5, second pass S/N ratio=2, and mass tolerance=0.5%. Peaks were labeled automatically by their mass-to-charge ratio (m/z). All peaks were subtracted from baseline, calibrated for mass accuracy, detected and clustered using the Biomarker Wizard® program. Normalized spectra for each of the profiles were compared on the basis of their intensity or normalized peak height. Data from Biomarker Wizard were exported for statistical analysis using SAS® software. Generalized estimating equations (GEE) with adjusted multiple comparisons were used to identify peaks for which there was evidence of statistically significant differences in the distribution of intensity scores among the replicates of uninfected and HIV-infected PM and MDM. The raw intensity values were found to be asymmetrical and adjusted prior to analysis using the arsinh transformation: $Y=\log_2(X+\sqrt{X^2+1})$, where 'X' is the observed intensity. This transformation has been used previously to stabilize intensity variance and make data more nearly normally distributed, and it has the advantage over a log-transformation of being able to handle negative intensities. An "adjusted p-value" (a "q-value") was computed to address the issue of multiple comparisons, by which the false discovery rate was controlled at 0.05 (i.e., no more than 5% expected false positives out of differentially expressed ones).

For the Western blot analyses, an un-paired two-tailed student's t-test was used to compare the densitometry values of the blots obtained from Quantity One Software and illustrated as mean plus SEM. ANOVA was used to compare cell viability results. Unpaired Student's t-test was used for the evaluation of HIV p24 antigen levels of the small interfering RNA assays.

The results according to the invention will be described in accordance with the description below and the accompanying Figures.

HIV infection of PM and MDM was demonstrated by determining the levels of p24 antigen per time in culture from three different donors (open circles) and PM from six different donors (solid circles) where used. HIV-infected donors showed differences in HIV replication during six days after viral infection.

Figure 1A:
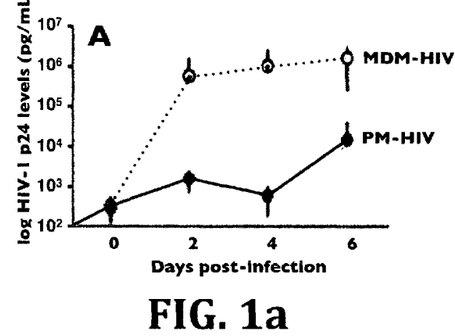
FIG. 1a shows a combined lineal graphic showing the HIV infection of PM and MDM according to the invention.
Figure 1B:
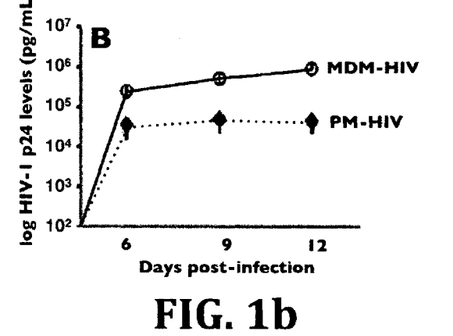
FIG. 1b shows another combined lineal graphic showing the HIV infection of PM and MDM according to the invention.

PM showed significantly lower levels of p24 antigen than did MDM regardless of donor (p=0.001) as shown in FIG. 1a. The differences were ~2 logs from 2 to 12 days post-infection and confirmed previous observations that were made in our laboratory. Experiments using MDM and PM cell supernatants cultured for 12 days after infection as seen on FIG. 1b showed that PM remains restrictive for HIV by determining the levels of p24 antigen per time in culture. In vitro infection of four different MDM and PM donors were cultured 12 days post-infection.

Cytopathology was not observed in uninfected cultures. We used 6-day lysates from uninfected PM and HIV-infected PM for proteomics studies to compare uninfected MDM and HIV-infected MDM at the same time-point.

Figure 2:
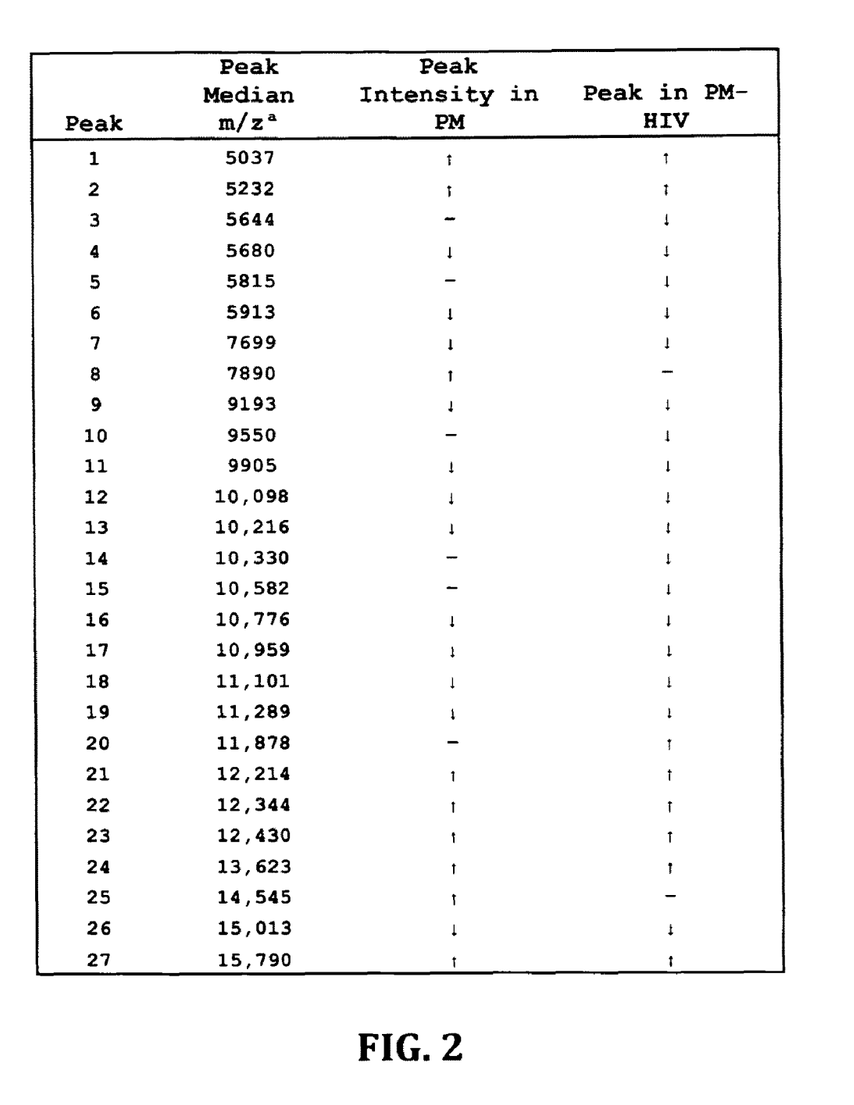
FIG. 2 shows a tabulated table of SELDI-TOF protein peaks in uninfected and HIV-infected PM according to the invention.
Figure 3:
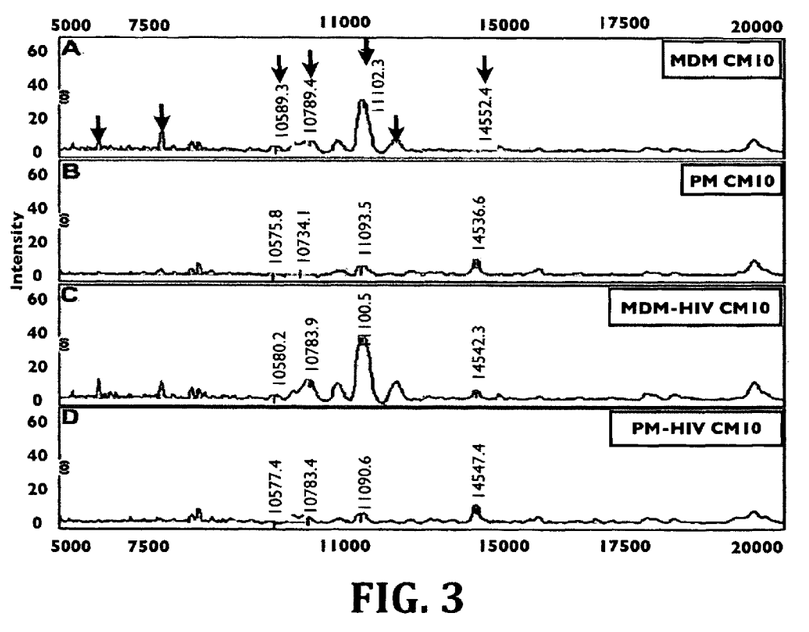
FIG. 3 shows SELDI-TOF spectra of 6-days uninfected and HIV-infected MDM and PM lysates using weak cation-exchange chips (CM-10) according to the invention.

SELDI-TOF profiling with the cationic and anionic chips CM-10 and Q-10, respectively, demonstrated spectral differences between 6-day lysates of PM and MDM. Protein spectra of HIV-infected PM and MDM were investigated using CM-10 chips and it showed increased peak numbers and higher peak intensities than those observed with Q-10 chips. Based on these results, comparisons between the two cell groups following viral infection were done with CM-10 chips. Biomarker Wizard analysis identified a total of 99 peaks between the uninfected and HIV-infected cell lysates. Following GEE statistical analyses and multiple comparisons adjustment to control for false positives, 27 proteins were found differentially expressed in uninfected or HIV-infected PM and MDM as shown in FIG. 2. Of these, 12 protein peaks (numbers 4, 6, 7, 9, 11-13, 16-19, and 26) showed lower intensities in both PM and PM-HIV than in MDM and MDM-HIV. In addition, seven peaks (numbers 1, 2, 21-24, and 27) had higher intensities in PM and PM-HIV than in MDM and MDM-HIV. Two protein peaks (numbers 8 and 25) were higher in PM than in MDM but were not detected in HIV-infected PM or HIV-infected MDM. Five protein peaks (numbers 3, 5, 10, 14, and 15) were lower in HIV-infected PM than in HIV-infected MDM but were not detected in uninfected cell lysates. One protein peak (number 20) was found only in infected cells and was up-regulated in PM-HIV over MDM-HIV. Representative spectra showing several differentially expressed protein peaks with m/z of 11,101, 10,582, 14,545, and 10,776 are shown in FIG. 3. The differentially expressed peaks in MDM and PM with m/z of 10,582, 10,800, and comparison of MDM and PM showed that the 11,102 m/z peak had significally lower intensity in PM (p=0.0004).

These peaks may represent the same peptide or may represent more than one protein with similar molecular masses given that the SELDI-TOF technology platform has relatively low resolution. The LC-MS/MS peptide sequencing is more sensitive and specific, and provides quite accurate information about protein I.D. and relative abundance. Therefore, after discovering significant differences in the protein profiles between uninfected and HIV-infected PM and MDM, we proceeded to identify the proteins by LC-MS/MS within the molecular weight range detected from the SELDI-TOF profiling (5-20 kDa).

Figure 4:
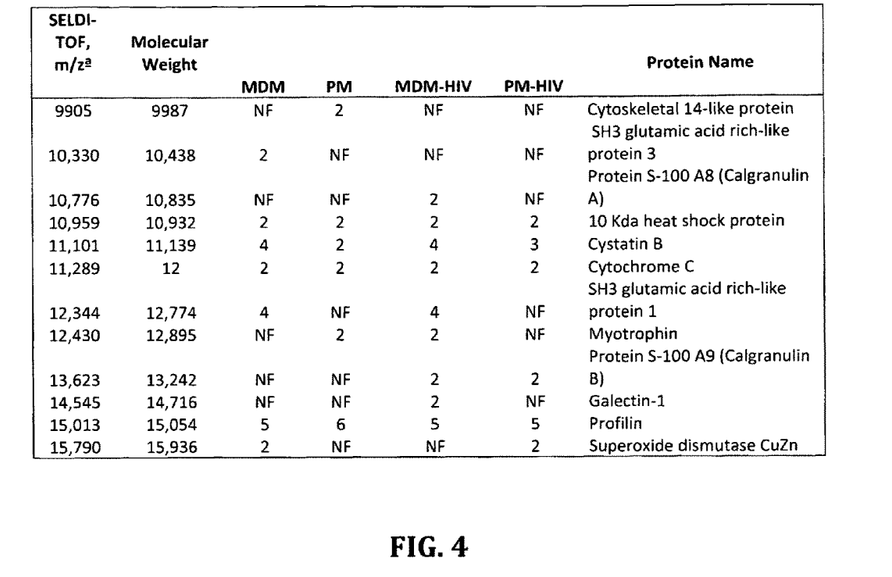
FIG. 4 is a table that presents the comparison of SELDI protein peaks and LC-MS/MS sequencing data.

One-dimensional (1D) SDS PAGE was used to fractionate proteins in the 5-20 kDa range. This experiment was designed to identify proteins whose molecular masses corresponded to SELDI-TOF peaks showing significant differences in intensities. After 1D protein separation, regions of the gel corresponding to the molecular weights identified in the SELDI-TOF spectra were excised and digested with trypsin. The resulting peptides were sequenced by LC-MS/MS and theoretical molecular weights of identified proteins derived from the NCBI database were compared to SELDI-TOF peaks as shown in FIG. 4. This method identified 12 proteins within the mass range of SELDI-TOF profiling with the theoretical molecular weight provided by the NCBI database corresponding to peaks 11, 14, 16-19, and 22-27 in SELDI-TOF analysis as shown in FIG. 2. Spectral differences were demonstrated in FIG. 2, between 6-day lysates of PM and MDM. SELDI-TOF statistical analyses of protein profiles in uninfected PM compared to MDM. All peaks showing ↓ relationship have decreased intensity and those with ↑ have increased intensity and all have adjusted p≦0.05. SELDI-TOF statistical analyses of protein in HIV-infected PM compared to HIV-infected MDM.

These proteins were identified as cytoskeletal 14-like protein, SH3 glutamic acid rich-like protein 3, protein S-100 A8 (also known as calgranulin A), 10 kDa heat shock, cystatin B, cytochrome C, SH3 glutamic acid rich-like protein 1, myotrophin, protein S-100 A9 (also known as calgranulin B), galectin-1, profilin, and superoxide dismutase CuZn (SOD). Of these, CSTB (MW: 11,139Da) was selected for further analysis because its differential expression in uninfected and HIV-infected PM and MDM correlated well with SELDI-TOF profiling, 1D-gel electrophoresis, mass spectrometry measurements, and previous studies have identified this protein as increased in HIV-infected MDM supernatants when compared to uninfected MDM as shown in FIG. 3 and FIG. 4. We also choose SOD for validation because a peak corresponding to a similar m/z (peak 27 in FIG. 2 was significantly increased in uninfected and HIV-infected PM over MDM and because in the same study we identified that this protein was up-regulated in supernatants of HIV-infected MDM as compared with uninfected controls.

Figure 5A:
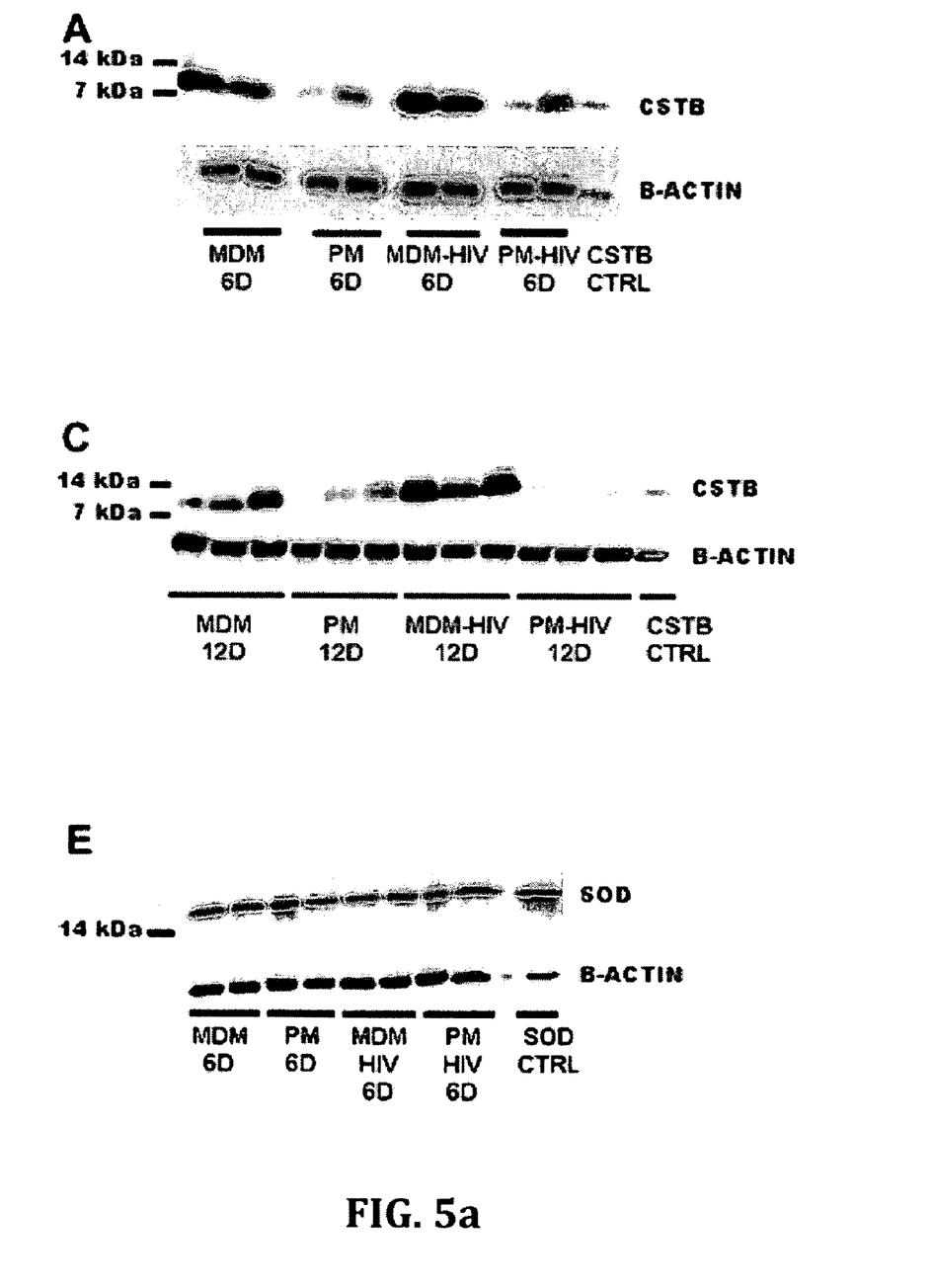
FIG. 5a shows a Western Blot Plotting that illustrates the difference in cystain B expression between uninfected (MDM and PM) and HIV-infected (MDM-HIV and PM-HIV) according to the invention.

We performed Western blotting to validate the expression of CSTB and SOD. We found that the relative abundance of CSTB was higher in MDM than in PM at 6 and 12 days post-infection (FIG. 5a, plot A and plot C, respectively). In FIG. 5a, normalized densitometry of 6-day and 12 day lysates (panels B and D) shows that the CSTB protein band is more abundant in uninfected MDM than in PM (p=0.0008 and p=0.008) and is more abundant in 6-day and 12-day lysates from MDM-HIV than n those from PM-HIV (p=0.0003) and p=<0.0001). Cell lysates from four and three different donors were blotted and probed in three independent blots against CSTB (panels A and C) and SOD (panel E) respectively. MDM (panel A and C) had higher CSTB levels than did PM. MDM-HIV (panels A and C) expressed more CSTB that did PM-HIV. Blots of SOD (panel E) showed no significant difference between tested samples, and were validated by densitometry of normalized blots (panel F). In addition, HIV-infected MDM have higher CSTB levels than uninfected MDM (p=0.009, panels C and D).

Figure 5B:
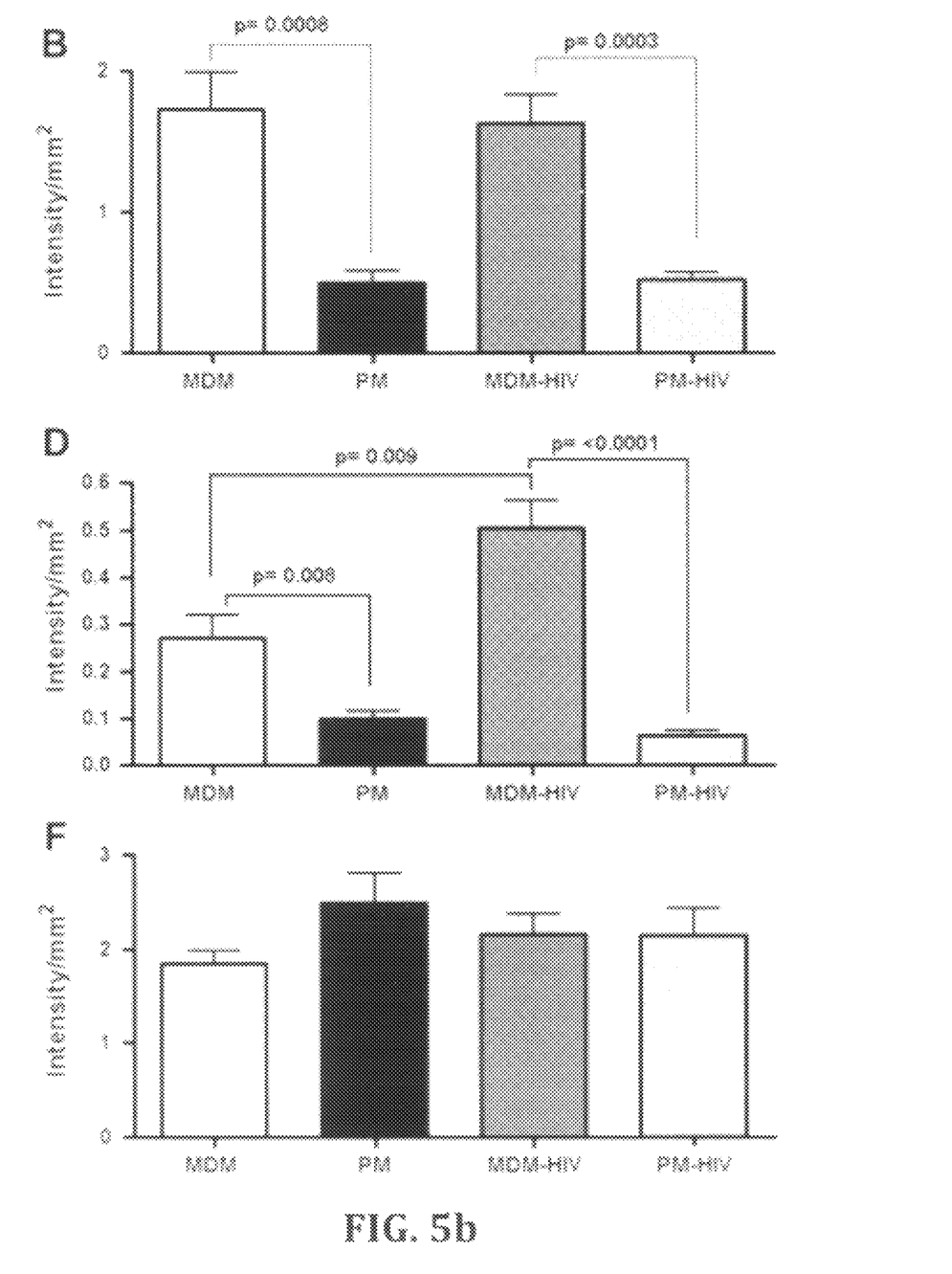

This finding was further confirmed by quantitative densitometry as statistically significant (p=0.0006 and p=0.008, FIG. 5b, plot B and plot D, respectively). CSTB was more abundant in HIV-infected MDM at 6 and 12 days post-infection than in infected PM (FIG. 5a, plot A and plot C, respectively) further confirmed by densitometry analysis (p=0.0002 and p=<0.0001, FIG. 5b, plot B and plot D, respectively). In addition, HIV-infected MDM have up-regulated expression of CSTB, as compared with uninfected MDM, at 12 days post-infection (p=0.009, FIG. 5a, plot C and FIG. 5b, plot D, respectively). However, SOD Western blotting showed no difference between uninfected and HIV-infected MDM and PM (FIG. 5a, plot E). Densitometry further confirmed equal amounts of SOD in the groups (FIG. 5b, plot F). β-Actin, which was used as an internal control, showed an equivalent protein content among all samples. The pattern of CSTB expression found in Western blots (FIG. 5a, plot A) corresponded to the differentially expressed peak with m/z of 11,101 by SELDI-TOF profiling presented in FIG. 3 for the uninfected and infected lysates, respectively, and to the amount of detected peptides in the sequencing as shown in FIG. 4. These results confirmed the differential expression of CSTB in PM, as compared with MDM.

Figure 6A:
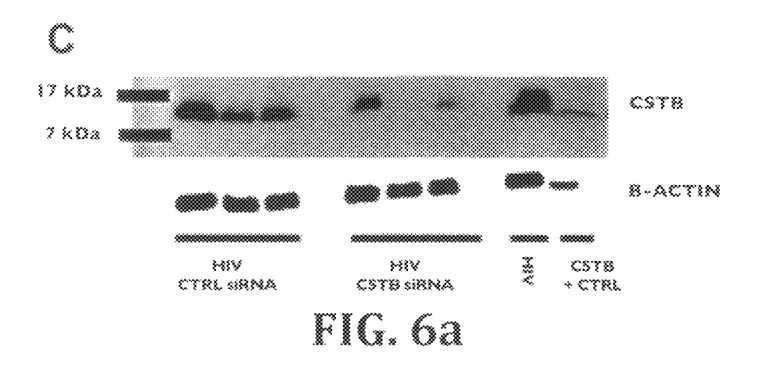
FIG. 6a is a representative Western Blots showing the levels of HIV p24 antigen and cell viability measured in cells treated with control siRNA, CSTB siRNA, and untreated HIV-infected cells according to the invention.
Figure 6B:
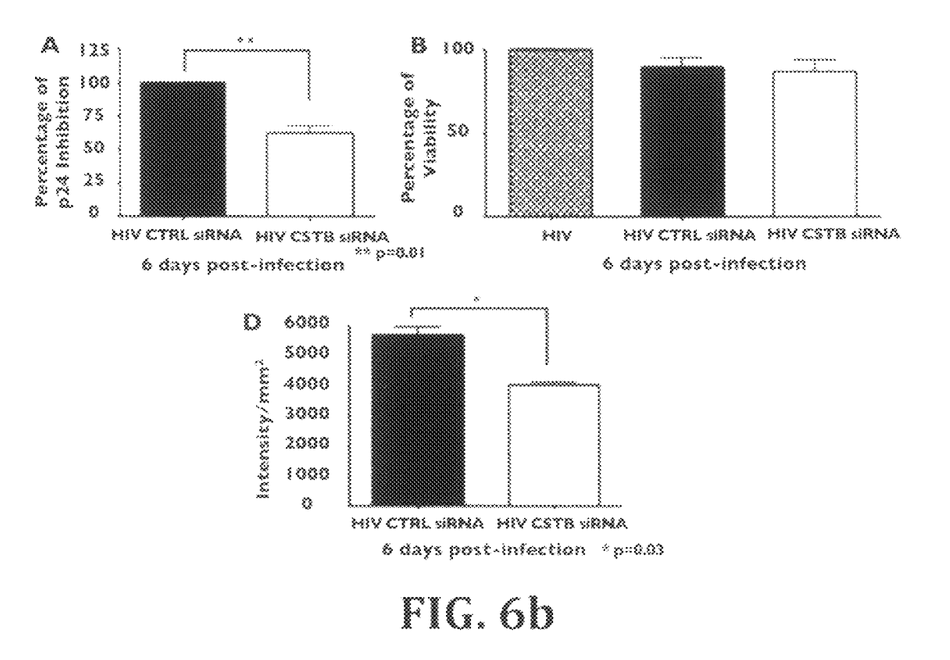
FIG. 6b illustrates a Bar chart showing statically the effect of silencing of CSTBby siRNA on HIV replication in MDM according to the invention.

To determine the effect of CSTB on HIV replication, MDM were transfected with CSTB siRNA followed by infection for 6 days. Levels of HIV p24 antigen and cell viability were measured in cells treated with control siRNA, CSTB siRNA, and untreated HIV-infected cells. We compared the levels of HIV between siRNA- and CSTB siRNA-treated cells as previously reported and found that HIV replication decreased significantly in CSTB siRNA-treated MDM (p=0.01, FIG. 6b, plot A). Cell viability was not affected in untreated HIV-infected, control siRNA-treated, and CSTB siRNA-treated cells (p=0.2466) as compared to untreated control (FIG. 6b, plot B). We measured the expression of CSTB in whole cell lysates to determine if silencing abrogated protein expression in MDM. As shown in representative Western blot, CSTB siRNA-treated samples showed a decreased protein expression as compared with control siRNA- as shown in FIG. 6a. These differences were specific to the cells treated with CSTB siRNA as the β-actin shows similar protein content among all the samples. Densitometry analysis of Western blot assays confirmed the reduction of cystatin B in CSTB siRNA-treated samples as significant (FIG. 6b, plot D; p=0.03). Densitometry analysis further demonstrated that HIV-infected MDM CSTB siRNA-treated samples have a lower CSTB protein expression than HIV-infected control siRNA (panel D, p=0.03).

These results demonstrate that down-regulation of CSTB diminishes HIV replication and confers the MDM low permissiveness to the virus, producing a 40% reduction in p24 antigen levels. These results suggest that low CSTB levels diminish the permissiveness of macrophages to HIV infection.

Our study found differences in the levels of CSTB between PM and MDM that are intrinsic to these cell populations and persist after viral infection. CSTB was identified from a large number of potential candidates: 27 protein peaks differentially expressed between uninfected and HIV-infected MDM and PM. We decided to focus on CSTB because this protein peak showed significant differences in intensity between uninfected and HIV-infected PM and MDM in the SELDI-TOF profiling and correlated with LC-MS/MS identification as demonstrated by the number of peptides found. We did not detect any differences between PM and MDM SOD levels by Western blots and LC-MS/MS. These results did not correspond to the up-regulation of the 15,790 m/z protein peak by SELDI-TOF in both uninfected and HIV-infected PM, as compared to MDM, thus suggesting that the difference observed in the SELDI-TOF protein peaks could correspond to a different protein with a similar mass as reported for SOD.

In addition, LC-MS/MS data suggests that SOD was present in MDM and PM-HIV as shown in FIG. 4, with similar number of identified protein peptides. Since the number of peptides identified in a particular sample does not always correlate with the actual protein expression, we decided to validate SOD protein expression by Western blots. In previous studies we found SOD differentially expressed in HIV-infected MDM supernatants; however, LC-MS/MS data identified this protein only in the uninfected controls. This finding emphasizes the pivotal importance of validation using techniques such as Western blotting or ELISA to perform a quantitative analysis of the protein content.

We also found three additional proteins differentially expressed in uninfected and HIV-infected PM and MDM. Some of these have been reported to be associated with HIV infection in both macrophages and T cells. These three are profilin, protein S-100 A9, and SH3 glutamic acid rich-like protein 1. Profilin was incorporated into virions and its secretion increased in parallel to productive HIV replication as determined by increased HIV p24 levels. The inhibitor of profilin, poly-1-proline, also inhibited virions progeny production, thus supporting the role of profilin in HIV replication. Using LC-MS/MS we found a similar number of peptides for profilin in all our samples. The SELDI-TOF profiling suggests that profilin was down-regulated in both PM and PM-HIV as compared with MDM and MDM-HIV. Future studies on profilin will determine if this protein has a role in HIV infection of PM. Calgranulin B, belongs to the myeloid-related proteins (MRPs) that are recently found to induce HIV production in a lymphoid cell line. In addition, it usually forms heterodimers with calgranulin A, another member of the MRPs, which was found incorporated in HIV viral progeny. We detected calgranulin A and B proteins by LC-MS/MS in the HIV-infected PM and MDM, respectively, suggesting the up-regulation of these proteins upon HIV infection. SH3 glutamic acid rich-like protein 1 belongs to the thioredoxin-like protein superfamily. The thioredoxin system is composed of several proteins, among them the peroxiredoxins, reported to inhibit HIV replication when T cells are treated with recombinant proteins. The exact role of these proteins should be further analyzed in both MDM and PM because previous reports were focused on T cells or on lymphoid cell lines. It remains to be determined what role these three additional proteins play in HIV replication in the placenta.

The inventors believe to be the first to show the differential expression of CSTB in PM and MDM. Cystatin family members are cysteine proteinase inhibitors. Type 1 cystatins, which include forms A and B, are intracellular molecules. In the placenta, cystatins control the protease activity of cathepsins, which are required for placental development and normal embryogenesis. In particular, CSTB is responsible for the control of cathepsins B and L, and imbalances in the cathepsin-cystatin system that play an important role in miscarriage. Cathepsins contribute to placental angiogenesis, embryo development, and uterine decidualization. Their role is thought to be the regulation of trophoblasts' invasion into the maternal decidua, which is necessary for the establishment of the placenta. Cathepsin L produced by trophoblasts is present occasionally in term placenta but at high levels in the first trimester. This protein was found to be down-regulated in term placenta and its expression associated with macrophages. Because of the close relationship between trophoblasts and PM, we postulate that the down-regulation of CSTB found in our study could naturally be down-regulated at term because of the low levels of the cathepsins. CSTB down-regulation may be an innate mechanism that affects viral permissiveness by yet unknown mechanisms. However, to the best of our knowledge there are no published reports on the exact identity of the cells producing CSTB in placenta.

Down-regulation of CSTB in HIV highly permissive MDM decreased viral replication in MDM, but how this is achieved remains unknown. This study suggests that low levels of CSTB in PM could contribute to HIV restriction in these macrophages. However, other mechanisms also contribute to the low permissiveness of placental macrophages such as the low CCR5 receptor expression reported previously by our group and the presence of known HIV restrictive factors such as LIF. Assessment of LIF in PM could provide important information regarding other known inhibitory factors that could be operating in the complex mechanisms underlining PM restriction of HIV. Further studies will be conducted to determine the exact signaling pathways of CSTB in PM restriction of HIV.

This invention is very significant as it offers the first analysis of the low molecular weight proteome of the PM and suggests a new role for CSTB in HIV replication. Synthetic inhibitors of CSTB could provide important protection against HIV replication, in addition to combined antiretroviral therapies, by blocking primary HIV infection in macrophages and limiting viral spread. If HIV replication is attenuated or decreased by means of interfering with CSTB expression, we could possibly reduce to some extent the infection of macrophage reservoirs and control more efficiently HIV infection.

We claim:

1. A method of reducing HIV-Replication in human body tissue comprising specifically down regulating expression of Cystatin B gene in said human body tissue with a nucleic acid inhibitor.

2. The method of claim 1, where in said human body tissue comprises a placenta.

3. The method of claim 1, wherein said nucleic acid inhibitor is siRNA.

* * * * *